US011020118B2

(12) United States Patent
Hwang et al.

(10) Patent No.: US 11,020,118 B2
(45) Date of Patent: Jun. 1, 2021

(54) PERIPHERAL NERVE FIXING APPARATUS

(71) Applicant: KOREA INSTITUTE OF SCIENCE AND TECHNOLOGY, Seoul (KR)

(72) Inventors: Donghyun Hwang, Seoul (KR); Keehoon Kim, Seoul (KR); Yong Seok Ihn, Seoul (KR); Sehyuk Yim, Seoul (KR); Jinwoo Jeong, Seoul (KR); Sang Rok Oh, Seoul (KR); Kyung Su Park, Seoul (KR); Sung Hwa Choi, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 101 days.

(21) Appl. No.: 16/287,246

(22) Filed: Feb. 27, 2019

(65) Prior Publication Data
US 2019/0314023 A1 Oct. 17, 2019

(30) Foreign Application Priority Data

Apr. 13, 2018 (KR) .................. 10-2018-0043058

(51) Int. Cl.
*A61B 17/11* (2006.01)
*A61B 5/00* (2006.01)
(Continued)

(52) U.S. Cl.
CPC ........ *A61B 17/1128* (2013.01); *A61B 5/4041* (2013.01); *A61B 5/4893* (2013.01);
(Continued)

(58) Field of Classification Search
CPC ...... A61B 17/1128; A61B 2017/00561; A61B 2017/0556; A61B 2017/00566;
(Continued)

(56) References Cited

U.S. PATENT DOCUMENTS 4,306,561 A 12/1981 Medinaceli
6,007,523 A * 12/1999 Mangosong .................. 604/540
(Continued)

FOREIGN PATENT DOCUMENTS

KR 10-2005-0045643 A 5/2005
KR 10-0942226 B1 2/2010
(Continued)

OTHER PUBLICATIONS

Yelena Akelina, "Microsurgical Technique for 1 mm Vessel End to End Anastomosis", Journal of Medical Insight, 2014 Abstract.
(Continued)

*Primary Examiner* — Ashley L Fishback
*Assistant Examiner* — Uyen N Vo
(74) *Attorney, Agent, or Firm* — Rabin & Berdo, P.C.

(57) ABSTRACT

Disclosed is a peripheral nerve fixing apparatus, which includes: a suction unit configured to provide a negative pressure to a peripheral nerve at an end portion thereof to fix the peripheral nerve; and a negative pressure generating unit having a vacuum pump for generating a negative pressure and connected to the suction unit so that the negative pressure is provided to the suction unit, wherein at one surface of the end portion of the suction unit, the suction unit includes: a fixing unit provided to contact the peripheral nerve to keep a stable fixed state; and a suction hole formed in the fixing unit so that the negative pressure is provided to the peripheral nerve therethrough.

9 Claims, 5 Drawing Sheets

(51) Int. Cl.
*A61B 5/02* (2006.01)
*A61N 1/05* (2006.01)

(52) U.S. Cl.
CPC ......... *A61B 5/02007* (2013.01); *A61B 5/6882* (2013.01); *A61N 1/0551* (2013.01)

(58) Field of Classification Search
CPC .... A61B 2017/1125; A61B 2018/1495; A61B 5/4041; A61B 5/4047; A61B 5/4052; A61B 5/4893; A61B 2017/00761; A61B 2017/00752; A61B 2018/00452; A61B 2018/00458; A61B 2018/0047; A61B 2018/00476; A61B 5/0051; A61B 18/14; A61N 1/0551; A61N 1/0529; A61N 1/06
USPC ........................................................ 600/204
See application file for complete search history.

(56) References Cited

U.S. PATENT DOCUMENTS

| | | | |
|---|---|---|---|
| 6,241,739 B1* | 6/2001 | Wadron | 606/131 |
| 6,383,134 B1* | 5/2002 | Santilli | A61B 17/0206 600/205 |
| 6,511,416 B1* | 1/2003 | Green, II | A61B 17/02 600/37 |
| 2002/0099270 A1* | 7/2002 | Taylor et al. | 600/204 |
| 2008/0188782 A1* | 8/2008 | Carkner | A61H 9/0078 601/151 |
| 2010/0168625 A1* | 7/2010 | Swain | A61B 17/1128 601/6 |
| 2010/0317925 A1* | 12/2010 | Banchieri | A61B 1/32 600/210 |
| 2011/0077690 A1 | 3/2011 | Shin et al. | |
| 2018/0104478 A1 | 4/2018 | Hwang et al. | |

FOREIGN PATENT DOCUMENTS

| | | |
|---|---|---|
| KR | 10-1684938 B1 | 12/2016 |
| KR | 10-1842618 B1 | 3/2018 |
| WO | WO 2005/046468 A1 | 5/2005 |

OTHER PUBLICATIONS

Jagannath B. Kamath et al., "Innovative Nerve Approximator From External Fixator: A Quick Fix Solution", Techniques in Hand & Upper Extremity Surgery, Sep. 2011, pp. 182-184, vol. 15, No. 3.

* cited by examiner

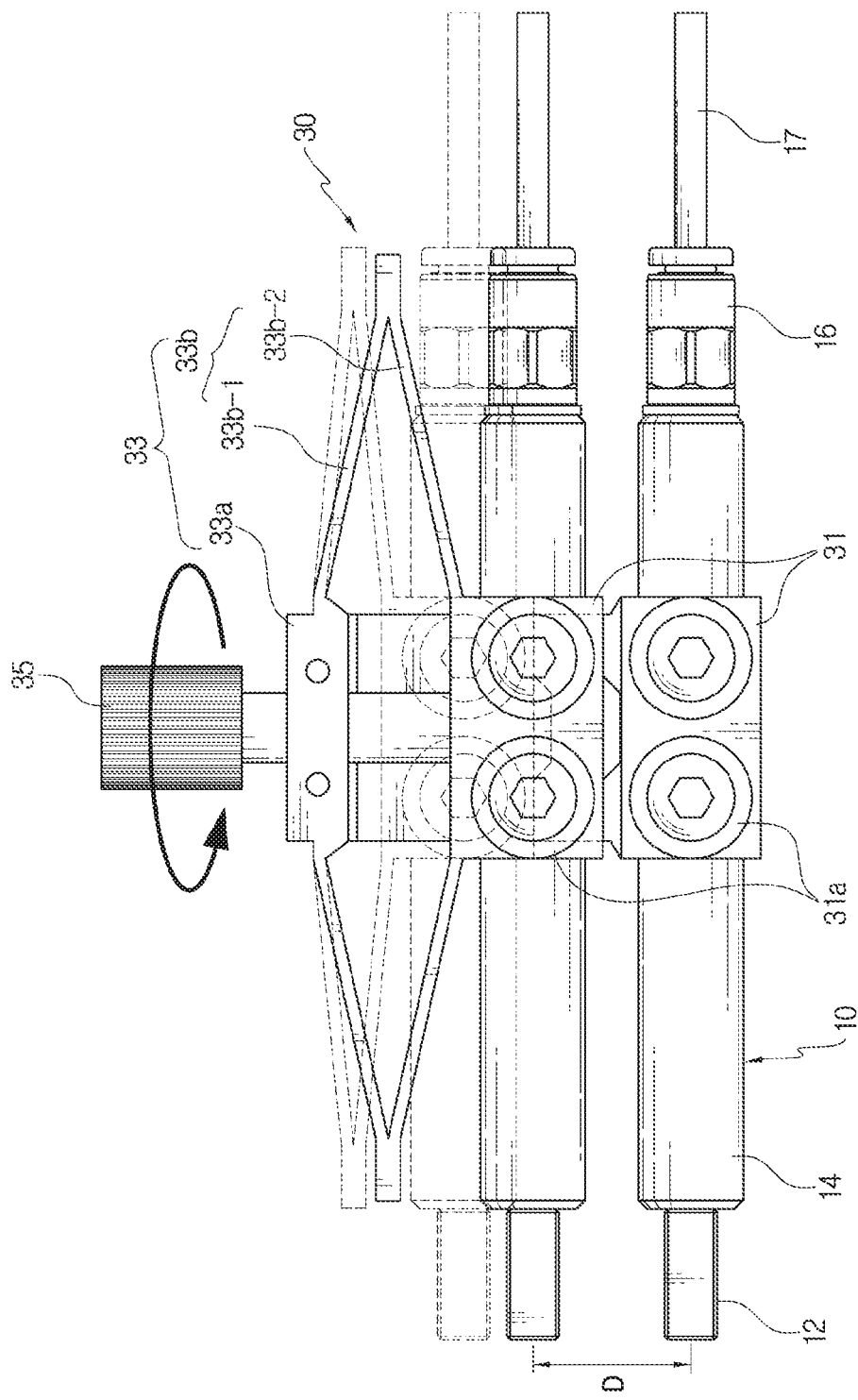

PERIPHERAL NERVE FIXING APPARATUS

CROSS-REFERENCE TO RELATED APPLICATION

This application claims priority to Korean Patent Application No. 10-2018-0043058, filed on Apr. 13, 2018, and all the benefits accruing therefrom under 35 U.S.C. § 119, the contents of which in its entirety are herein incorporated by reference.

STATEMENT REGARDING SPONSORED RESEARCH

This study was supported by the STEAM study (Bionic arm system having a bio-signal based control function, Project No. 1711058885) of Korea Research Foundation, the Ministry of Science, Technology and Information, Republic of Korea under the sponsorship of Korea Institute of Science and Technology.

BACKGROUND

1. Field

The present disclosure relates to a peripheral nerve fixing apparatus, and more particularly, to a peripheral nerve fixing apparatus capable of stably fixing a peripheral nerve by providing a negative pressure to the peripheral nerve.

2. Description of the Related Art

A peripheral nerve is a pathway that transmits the senses collected from body skins, skeletal muscles and various internal organs to the central nervous system and transmits the exercise stimulation of the central nervous system to them again. The peripheral nerve includes nerves for transmitting senses and nerves for transmitting exercise signals.

The peripheral nerve includes axons, myelin sheath and endoneurium, which serve as nerve fibers, and also includes perineurium, fascicle and epineurium, which include axons, myelin sheath and endoneurium. In addition, the nerve bundles of the peripheral nerve are flexible, the epineurium of the nerve bundles are slippery, and the micro nerve fibers are distributed inside the nerve bundles.

The peripheral nerve having this structure should be fixed in performing the nerve junction surgery, the peripheral nerve surgery using a surgery robot, or the in-vivo neuroscience studies for peripheral nerves.

In the prior art, there is known a technique of pressing a target tissue using clamps to fix the position of the target tissue, and adjusting the gap between the clamps by manually changing the positions of the clamps. If the device for fixing a target tissue as above is used for the nerve, the nerve fibers inside the nerve may be compressed to cause nerve crush injury.

In addition, in the case of a device for fixing the nerve using a needle, the needle penetrates the nerve, which may result in hemorrhage at the blood vessel inside the nerve and tearing of the nerve tissue and the outer membrane to cause neurological damage.

SUMMARY

The present disclosure is designed to solve the above problems, and therefore the present disclosure is directed to providing an apparatus for fixing a peripheral nerve while minimizing the damage applied to the peripheral nerve.

In one aspect, there is provided a peripheral nerve fixing apparatus, comprising: a suction unit configured to provide a negative pressure to a peripheral nerve at an end portion thereof to fix the peripheral nerve; and a negative pressure generating unit having a vacuum pump for generating a negative pressure and connected to the suction unit so that the negative pressure is provided to the suction unit, wherein at one surface of the end portion of the suction unit, the suction unit includes: a fixing unit provided to contact the peripheral nerve to keep a stable fixed state; and a suction hole formed in the fixing unit so that the negative pressure is provided to the peripheral nerve therethrough.

According to an embodiment of the present disclosure, the negative pressure generating unit may further include: a regulator connected to the vacuum pump to adjust an air pressure; and a valve connected to the regulator to control a flux or pressure of the air sucked from the suction unit.

The negative pressure generating unit may further include a filter unit connected to the valve to filter the air sucked from the suction unit.

According to another embodiment of the present disclosure, the suction unit may be provided in plural, and the peripheral nerve fixing apparatus may further comprise a distance adjusting unit configured to accommodate the plurality of suction units, the distance adjusting unit being elastically deformed when being pressed in one direction to adjust a distance between the plurality of suction units.

The distance adjusting unit may include: accommodation units formed upward from a base of the distance adjusting unit to fix the suction units; and a flexible mechanism connected to at least one of the accommodation units and elastically deformed by pressing to move the accommodation unit.

The flexible mechanism may include: a pressing guide unit configured to guide a pressing control unit so that a pressing force is provided to the accommodation unit; and an elastic unit connected to the pressing guide unit and elastically deformed to provide a pressing force to the accommodation unit or release the pressing force so that the accommodation unit is moved.

Both sides of the elastic unit may be made of first and second members configured so that a distance therebetween is adjustable, and the first and second members are connected to each other at both side ends thereof to intersect each other.

According to another embodiment of the present disclosure, the fixing unit may include protrusions formed to protrude to contact the peripheral nerve.

End portions of the protrusions may have a sharp needle shape, and the suction hole may be an elongated hole formed between the protrusions.

BRIEF DESCRIPTION OF THE DRAWINGS

FIG. 4 is a conceptual diagram showing an operation of the peripheral nerve fixing apparatus according to the present disclosure.

DETAILED DESCRIPTION

Hereinafter, the embodiments disclosed in this specification will be described in detail. Here, identical or similar components are denoted by identical or similar reference symbols and not described in detail again. In the following description, the word "unit" used in terms is selected or endowed only in consideration of ease naming and does not have any distinguishable meaning or role. In addition, in the following description of the embodiments of the present disclosure, any detailed description of related arts can be omitted if it is determined that the gist of the embodiments disclosed herein can be obscured by the same. Moreover, it should be understood that the accompanying drawings are just for better understanding of the embodiments disclosed herein and are not to be construed as limiting the scope of the present disclosure. The scope of the present disclosure should be understood as including all changes, equivalents and alternatives thereof.

Terms having an ordinal such as "first" and "second" can be used for explaining various components, but the components are not limited by the terms. These terms are just used for distinguishing any component from another.

In case it is mentioned that any component is "connected" to another component, the component may be connected directly to another component, but it should be understood that any other component can be further interposed between them.

The singular expressions are intended to include the plural forms as well, unless the context clearly indicates otherwise.

In this specification, the term such as "include" and "have" is just to specify the presence of features, integers, steps, operations, elements, parts or components thereof, stated in the specification, but does not preclude the presence or addition of one or more other features, integers, steps, operations, elements, parts or components thereof.

Figure 1:
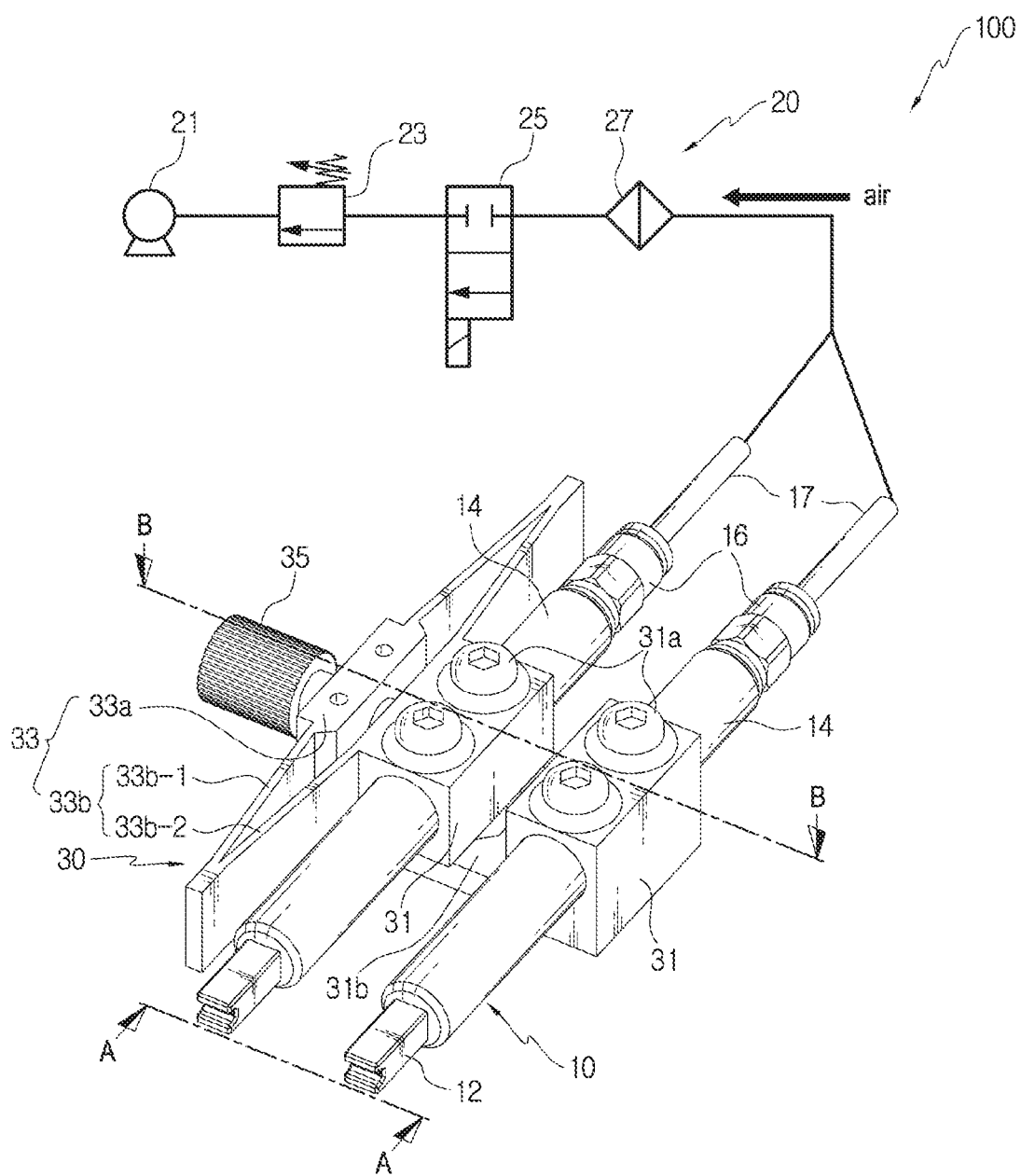
FIG. 1 is a conceptual diagram showing a peripheral nerve fixing apparatus according to the present disclosure.
Figure 2:
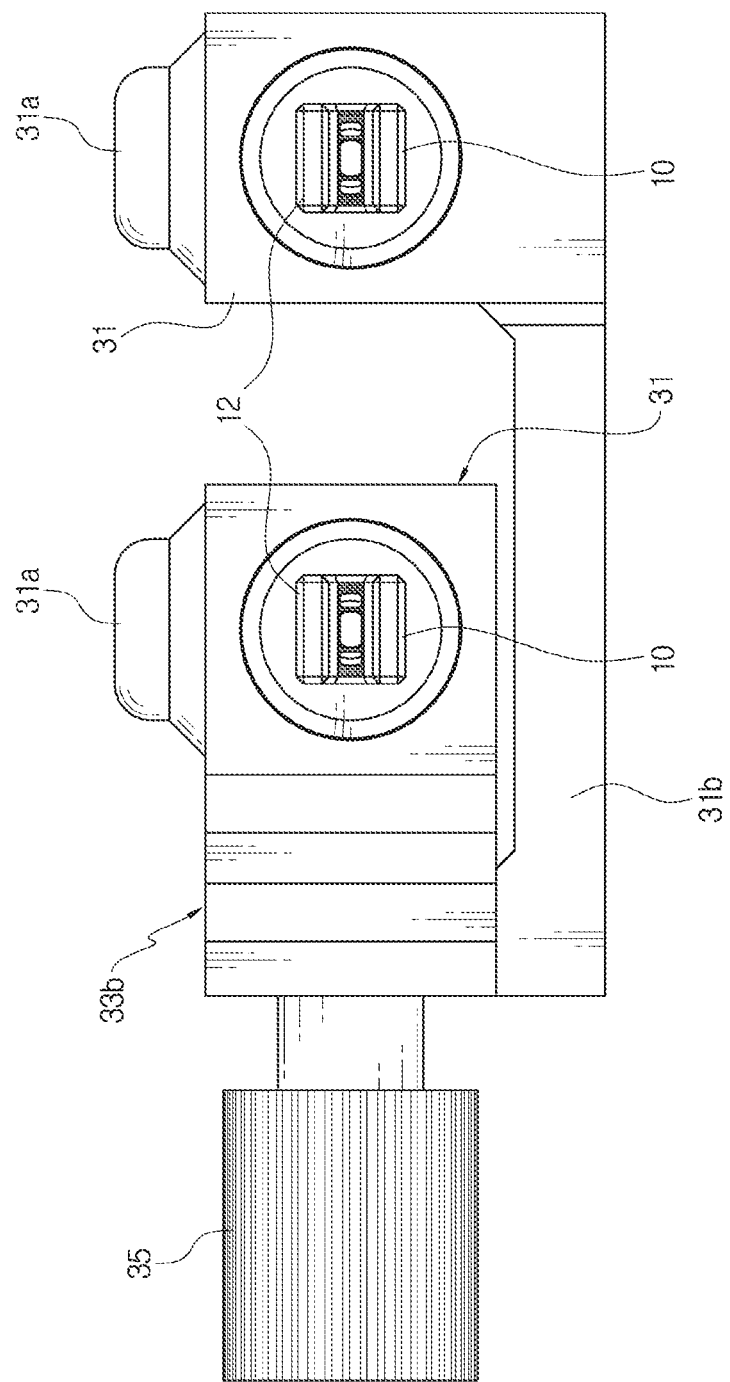
FIG. 2 is a side view, taken along the line A-A' of FIG. 1.
Figure 3A:
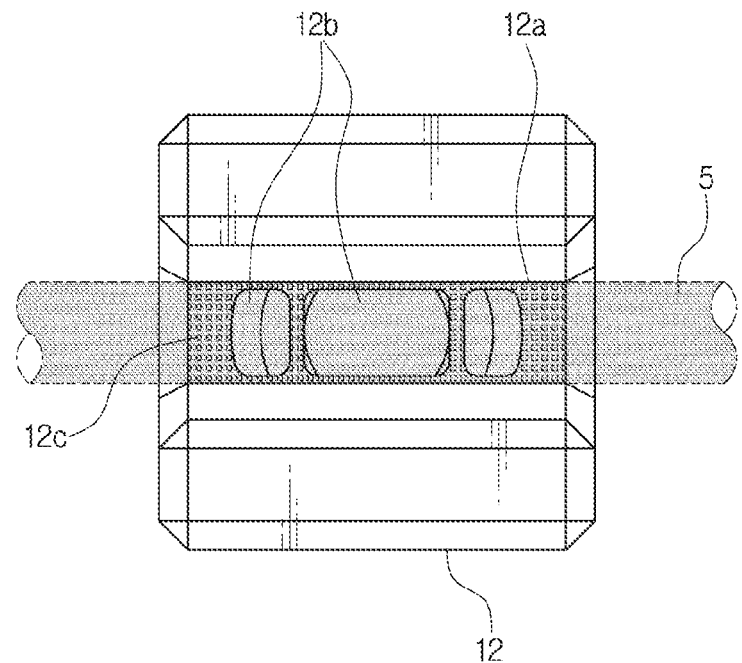
FIG. 3A is an enlarged front view showing an end portion of a suction unit.

FIG. 1 is a conceptual diagram showing a peripheral nerve fixing apparatus 100 according to the present disclosure, FIG. 2 is a side view, taken along the line A-A' of FIG. 1, and FIG. 3A is an enlarged front view showing an end portion 12 of a suction unit 10. Also, FIG. 3B is an enlarged side view showing the end portion 12 of the suction unit 10.

Hereinafter, the peripheral nerve fixing apparatus 100 of the present disclosure will be described with reference to FIGS. 1 to 3B.

The peripheral nerve fixing apparatus 100 of the present disclosure includes a suction unit 10 and a negative pressure generating unit 20.

Figure 3B:
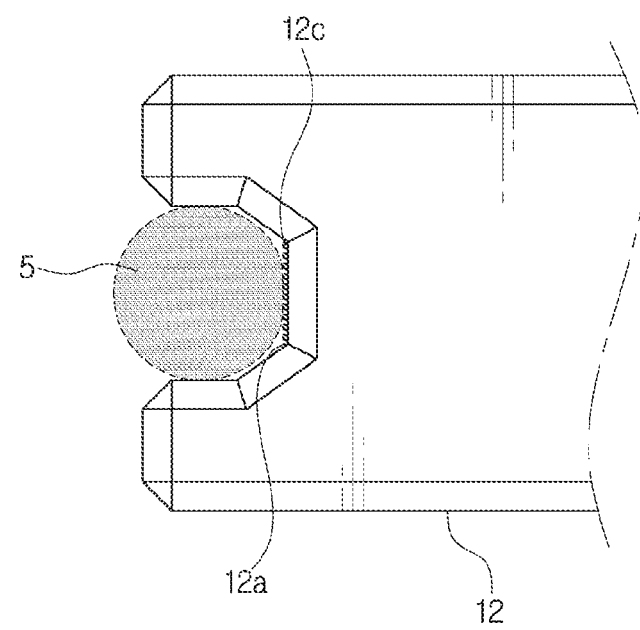
FIG. 3B is an enlarged side view showing the end portion of the suction unit.

The suction unit 10 is configured to provide a negative pressure to a peripheral nerve at an end portion 12 of the suction unit 10 to fix the peripheral nerve 5 (FIGS. 3A and 3B).

Referring to FIGS. 3A and 3B, at one surface of the end portion 12 of the suction unit 10, the suction unit 10 has a fixing unit 12a and a suction hole 12b.

The fixing unit 12a contacts the peripheral nerve 5 to keep a stable fixed state. For example, the fixing unit 12a may have protrusions 12c that are protruded to be contactable with the peripheral nerve. FIG. 3A shows an example where the protrusions 12c are provided at the fixing unit 12a to contact the peripheral nerve 5.

The suction hole 12b is formed to provide a negative pressure to the peripheral nerve. FIG. 3A shows an example where the suction hole 12b is formed between the protrusions 12c, but the present disclosure is not limited thereto.

Referring to FIG. 1, the suction unit 10 may include a pneumatic pipe 14, a hose 17, and a pneumatic fitting 16, which communicate with the end portion 12 of the suction unit 10. The pneumatic pipe 14 communicates with the end portion 12 of the suction unit 10 and the negative pressure generating unit 20 to maintain the pneumatic pressure and provide a negative pressure. The hose 17 is connected to the pneumatic pipe 14 by the pneumatic fitting 16. In this structure, the negative pressure generated by the negative pressure generating unit 20, explained later, may be supplied to the peripheral nerve through the end portion 12 of the suction unit 10.

The negative pressure generating unit 20 has a vacuum pump 21 for generating a negative pressure. Also, the negative pressure generating unit 20 is communicatively connected to the suction unit 10 to provide a negative pressure to the suction unit 10. For example, the negative pressure generating unit 20 may be connected to the suction unit 10 via a pipe. Since air is sucked in the direction of an arrow depicted in FIG. 1 by the vacuum pump 21, a negative pressure is generated. Referring to FIGS. 3A and 3B, the peripheral nerve is fixed at the end portion 12 of the suction unit 10.

Referring to FIG. 1, the negative pressure generating unit 20 may include a regulator 23 and a valve 25. The regulator 23 is connected to the vacuum pump 21 to adjust the air pressure of the sucked air. The valve 25 is connected to the regulator 23 and enables to control a flux or pressure of the air sucked from the suction unit 10.

The negative pressure generating unit 20 may further include a filter unit 27. The filter unit 27 is connected to the valve 25 to filter the air sucked from the suction unit 10, thereby blocking dust or various foreign substances. The filter unit 27 is detachably configured to be cleaned or replaced.

If the suction unit 10 is provided in plural, the peripheral nerve fixing apparatus 100 of the present disclosure may further include a distance adjusting unit 30 for adjusting a distance between the plurality of suction units 10. FIG. 1 shows an example where two suction units 10 are provided. However, the present disclosure is not limited thereto, and of three or more suction units may be provided. By means of the distance adjusting unit 30, the distance between the suction units 10 is adjusted in a lateral direction of FIG. 1.

The distance adjusting unit 30 may accommodate the plurality of suction units 10, and the distance adjusting unit 30 may be elastically deformed by being pressed in one direction to adjust the distance between the plurality of suction units 10.

The distance adjusting unit 30 may include an accommodation unit 31 and a flexible mechanism 33.

The accommodation unit 31 is formed upward from a base of the distance adjusting unit 30 to fix the suction unit 10. In addition, the flexible mechanism 33 is connected to at least one of the accommodation units 31 and is elastically deformed by pressing to move the accommodation unit 31.

Referring to FIGS. 1 and 2, a base portion 31a is formed at a bottom surface of one accommodation unit 31. Here, the accommodation unit 31 is movably disposed at the base portion 31a so that a relative distance between the plurality of accommodation units 31 may be adjusted. The base portion 31a may be formed to be connected to the accommodation units 31. FIG. 2 shows an example where the base portion 31a is connected to a left side of a right accommodation unit 31, and the base portion 31a is disposed at the bottom surface of the accommodation unit 31 so that the left accommodation unit 31 is movable. However, the present disclosure is not limited to this structure.

The flexible mechanism 33 may include a pressing guide unit 33a for guiding a pressing control unit 35 to provide a pressing force to the accommodation unit 31, and an elastic unit 33b connected to the pressing guide unit 33a and elastically deformed to provide a pressing force to the accommodation unit 31 or release the pressing force so that the accommodation unit 31 is moved.

A pressing control unit 35 may be installed at the pressing guide unit 33a. The pressing guide unit 33a may guide the rotation of the pressing control unit 35. The elastic unit 33b presses one accommodation unit 31 in an elastically deformed state to adjust the relative distance between the accommodation units 31. The pressing control unit 35 may be, for example, a knob, a bolt or a motor.

Referring to FIG. 1, the elastic unit 33b may include first and second members 33b-1, 33b-2. A distance between the first and second members 33b-1, 33b-2 may be adjusted, and the first and second members 33b-1, 33b-2 may be connected to each other at both side ends thereof to intersect each other. If the pressing guide unit 33a is pressed by the rotation of the pressing control unit 35, the first and second members 33b-1, 33b-2 move the accommodation unit 31 to adjust the relative distance between the suction units 10.

The operation of adjusting the relative distance between the suction units 10 will be described with reference to FIG. 4.

Referring to FIG. 4, if the pressing control unit 35 is rotated in one direction by a user, the end portion of the pressing control unit 35 presses one accommodation unit 31 to adjust the relative distance between the accommodation units 31 so that the accommodation units 31 become close to each other.

At this time, the elastic unit 33b is elastically deformed such that the relative distance between the first and second members 33b-1, 33b-2 is increased.

Meanwhile, if the pressing control unit 35 is rotated in a direction opposite to the one direction by the user, the pressed state of the end portion of the pressing control unit 35 to one accommodation unit 31 is released so that the relative distance between the accommodation units 31 is increased.

At this time, the elastic unit 33b is elastically deformed such that the relative distances between the first and second members 33b-1, 33b-2 is decreased.

Figure 5A:
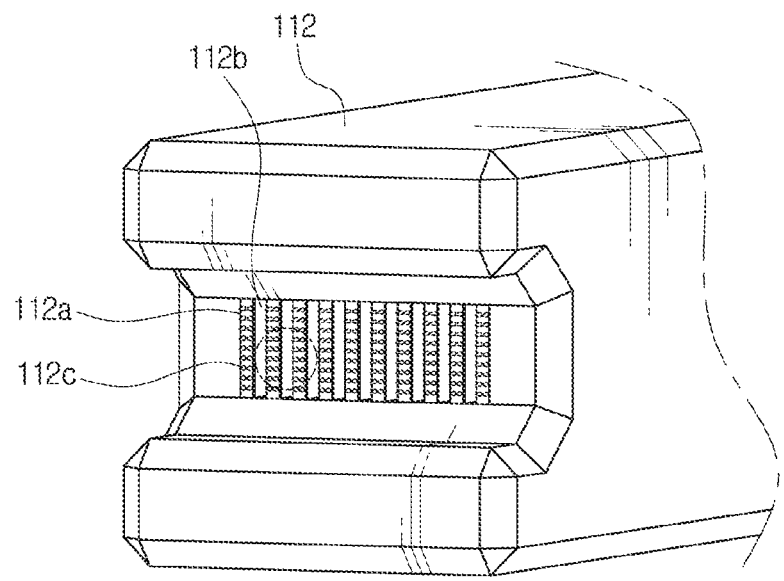
FIG. 5A is a perspective view showing a suction unit according to another embodiment.
Figure 5B:
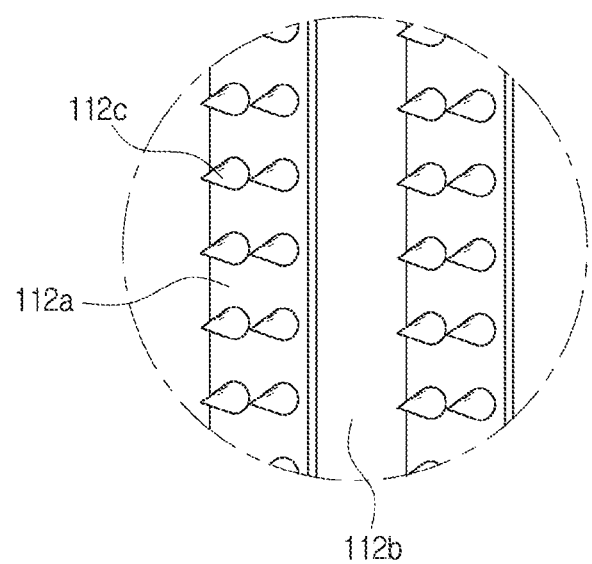
FIG. 5B is an enlarged view showing a protrusion and a suction hole of FIG. 5A.

FIG. 5A is a perspective view showing the suction unit 112 according to another embodiment. In the suction unit 112 of this embodiment, the end portion of the protrusion 112c has a sharp needle shape, and the suction hole 112b may be an elongated hole formed between the protrusions 112c having a sharp needle shape. FIG. 5B shows an example where the suction hole 112b is formed as an elongated hole extending vertically between the protrusions 112c.

The peripheral nerve fixing apparatus of the present disclosure may be used for surgeries for nerve segmenting and junction, and it is possible to fix the nerve while minimizing nerve damage. In addition, the peripheral nerve fixing apparatus of the present disclosure may be used as a nerve electrode insertion assistant device in the neuroscience field so that a nerve electrode may be implanted into the nerve. Meanwhile, the peripheral nerve fixing apparatus of the present disclosure may be used as an end effector of a microsurgical robot for micro-nerve surgery.

In the present disclosure, since the fixing unit is formed at the end portion of the suction unit and the suction hole allows a negative pressure to be provided to the peripheral nerve, it is possible to fix the peripheral nerve while minimizing the damage of the peripheral nerve.

In addition, in the present disclosure, since the fixing unit is protruded or has a needle structure to increase the frictional force, it is possible to maintain a stable fixed state against a lateral external force.

Meanwhile, in the present disclosure, since the flexible mechanism is elastically deformed by pressing to move the accommodation unit, it is possible to adjust the distance between the suction units that fix the peripheral nerve.

The peripheral nerve fixing apparatus 100 as described above are not limited to the configuration and method of the embodiments described above, but the embodiments may be modified in various ways by combining the embodiments entirely or selectively.

It will be apparent to those skilled in the art that the present disclosure can be embodied in other specific forms without departing from the essential characteristics of the present disclosure. Accordingly, the above detailed description should be considered in all respects as illustrative and not restrictive. The scope of the present disclosure shall be determined by rational interpretation of the appended claims, and all changes within the equivalence scope of the present disclosure shall fall within the scope of the present disclosure.

What is claimed is:

1. A peripheral nerve fixing apparatus, comprising:
a suction unit configured to provide a negative pressure to a peripheral nerve at an end portion thereof to fix the peripheral nerve; and
a negative pressure generating unit having a vacuum pump for generating a negative pressure and connected to the suction unit so that the negative pressure is provided to the suction unit,
wherein at one surface of the end portion of the suction unit, the suction unit includes:
a fixing unit provided to contact the peripheral nerve to keep a stable fixed state; and
a suction hole formed in the fixing unit so that the negative pressure is provided to the peripheral nerve therethrough;
wherein the peripheral nerve fixing apparatus further comprises a distance adjusting unit configured to accommodate a plurality of the suction units, the distance adjusting unit being elastically deformed when being pressed in one direction to decrease a distance between the plurality of the suction units; and
wherein the end portion of the suction unit comprises two prongs and a recess between the two prongs, the fixing unit being formed in a center of the recess.

2. The peripheral nerve fixing apparatus according to claim 1,
wherein the negative pressure generating unit further includes:
a regulator connected to the vacuum pump to adjust an air pressure; and
a valve connected to the regulator to control a flux or pressure of the air sucked from the suction unit.

3. The peripheral nerve fixing apparatus according to claim 2,
wherein the negative pressure generating unit further includes:

a filter unit connected to the valve to filter the air sucked from the suction unit.

4. The peripheral nerve fixing apparatus according to claim 1, wherein the distance adjusting unit is further configured to, in response to a release from being pressed in the one direction, increase the distance between the plurality of the suction units.

5. The peripheral nerve fixing apparatus according to claim 1,
wherein the distance adjusting unit includes:
accommodation units formed upward from a base of the distance adjusting unit to fix the suction units; and
a flexible mechanism connected to at least one of the accommodation units and elastically deformed by pressing to move the accommodation unit.

6. The peripheral nerve fixing apparatus according to claim 5,
wherein the flexible mechanism includes:
a pressing guide unit configured to guide a pressing control unit so that a pressing force is provided to the accommodation unit; and
an elastic unit connected to the pressing guide unit and elastically deformed to provide a pressing force to the accommodation unit or release the pressing force so that the accommodation unit is moved.

7. The peripheral nerve fixing apparatus according to claim 1,
wherein the fixing unit includes protrusions formed to protrude to contact the peripheral nerve.

8. The peripheral nerve fixing apparatus according to claim 7, wherein
the protrusions extend from the one surface of the end portion of the suction unit, and
end portions of the protrusions have a sharp needle shape, and the suction hole is an elongated hole formed in the one surface between the protrusions.

9. A peripheral nerve fixing apparatus, comprising:
a suction unit configured to provide a negative pressure to a peripheral nerve at an end portion thereof to fix the peripheral nerve; and
a negative pressure generating unit having a vacuum pump for generating a negative pressure and connected to the suction unit so that the negative pressure is provided to the suction unit,
wherein at one surface of the end portion of the suction unit, the suction unit includes:
a fixing unit provided to contact the peripheral nerve to keep a stable fixed state; and
a suction hole formed in the fixing unit so that the negative pressure is provided to the peripheral nerve therethrough;
wherein the peripheral nerve fixing apparatus further comprises a distance adjusting unit configured to accommodate a plurality of the suction units, the distance adjusting unit being elastically deformed when being pressed in one direction to decrease a distance between the plurality of the suction units;
wherein the distance adjusting unit includes:
accommodation units formed upward from a base of the distance adjusting unit to fix the plurality of the suction units; and
a flexible mechanism connected to at least one of the accommodation units and elastically deformed by pressing to move the accommodation unit;
wherein the flexible mechanism includes:
a pressing guide unit configured to guide a pressing control unit so that a pressing force is provided to the accommodation unit; and
an elastic unit connected to the pressing guide unit and elastically deformed to provide a pressing force to the accommodation unit or release the pressing force so that the accommodation unit is moved; and
wherein sides of the elastic unit are made of first and second members configured so that a distance therebetween is adjustable, and the first and second members are connected to each other at side ends thereof to intersect each other.

* * * * *